United States Patent
Abuzaina et al.

(10) Patent No.: US 7,310,145 B2
(45) Date of Patent: Dec. 18, 2007

(54) APPARATUS AND METHOD FOR DETERMINING OPTICAL RETARDATION AND BIREFRINGENCE

(75) Inventors: Ferass Abuzaina, Brooklyn, NY (US); Saša Andjelić, New York, NY (US); Benjamin D. Fitz, Brooklyn, NY (US)

(73) Assignee: Ethicon, Inc., Somerville, NJ (US)

( * ) Notice: Subject to any disclaimer, the term of this patent is extended or adjusted under 35 U.S.C. 154(b) by 356 days.

(21) Appl. No.: 10/784,573

(22) Filed: Feb. 23, 2004

(65) Prior Publication Data

US 2005/0184239 A1   Aug. 25, 2005

(51) Int. Cl.
*G01J 4/00* (2006.01)

(52) U.S. Cl. .................................... 356/365

(58) Field of Classification Search ................ 356/365, 356/368
See application file for complete search history.

(56) References Cited

U.S. PATENT DOCUMENTS

| | | | |
|---|---|---|---|
| 4,309,110 | A | 1/1982 | Tumerman |
| 4,668,086 | A | 5/1987 | Redner |
| 5,406,371 | A | 4/1995 | Sakai et al. |
| 5,825,492 | A | 10/1998 | Mason |
| 5,864,403 | A | 1/1999 | Ajji et al. |
| 6,480,277 | B1 * | 11/2002 | Nafie ........................ 356/364 |

FOREIGN PATENT DOCUMENTS

| | | |
|---|---|---|
| GB | 2 052 049 A | 1/1981 |
| GB | 2 068 458 A | 7/1981 |

OTHER PUBLICATIONS

Roche, E.J. et al., "Automated Digital Analysis of Fiber Interferograms", Textile Research Journal, Jul. 1987, pp. 371-378.

Takahashi, Tsutomu, et al. "Stress tensor measurement using birefringence in oblique transmission", Rheologica Acta, 1996, pp. 297-302, vol. 35, No. 4.

Abetz, V. et al., "Two-color rotary modulated flow birefringence", Rheologica Acta, 1990, pp. 11-15, vol. 29, No. 1.

Hamza, A. A. et al., "Interferometric determination of the optical anisotropy of poly(p-oxybenzoate-co-p-phenylene isophthalate) 50/50 composition fibres", Polymer Communications, 1989, pp. 188-189, vol. 30.

Marsh, R.D.L. et al., "Dynamic Optical Birefringence New possibilities in polymer characterisation", Journal of Thermal Analysis, 1995, pp. 891-902, vol. 45, John Wiley & Sons, Ltd.

Beekmans, F. et al., "Determination of Orientation in Thermotropic Liquid Crystalline Polymer Films by Spectrographic Measurement of the Birefringence", Macromolecules 1996, pp. 8726-8733, vol. 29, No. 27.

Hongladarom, K. et al., "Measurement of the Full Refractive Index Tensor in Sheared Liquid Crystalline Polymer Solutions", Macromolecules 1994, pp. 483-489, vol. 27, No. 2.

(Continued)

*Primary Examiner*—Roy M. Punnoose

(57) ABSTRACT

A method for determining the optical retardation and birefringence values of an anisotropic material utilizing a Fourier transform near infrared spectrophotometer operated in at least a portion of the range of wavenumbers between about 4,000 to about 10,000 $cm^{-1}$.

15 Claims, 8 Drawing Sheets

OTHER PUBLICATIONS

Hongladarom, K. et al., "Molecular Alignment of Polymer Liquid Crystals in Shear Flows. 1. Spectrographic Birefringence Technique, Steady-State Orientation, and Normal Stress Behavior in Poly(benzyl glutamate) Solutions", Macromolecules, 1993, pp. 772-784, vol. 26, No. 4.

Hongladarom, K. et al., "Molecular Alignment of Polymer Liquid Crystals in Shear Flows. 2. Transient Flow Behavior in Poly(benzyl glutamate) Solutions", Macromolecules, 1993, pp. 785-794, vol. 26, No. 4.

Yeh, Fengji, et al., "In-Situ Studies of Structure Development during Deformation of a Segmented Poly(urethane-urea) Elastomer", Macromolecules 2003, pp. 1940-1954, vol. 38, No. 6.

Mortimer, S.A. et al., "A Device for On-Line Measurement of Fiber Birefringence", Textile Research Journal, 1994, pp. 544-551, vol. 84, No. 9.

Yang, H.H. et al., "Birefringence of Highly Oriented Fibers", Journal of Polymer Science 1982, pp. 981-987, vol. 20, John Wiley & Sons, Inc.

* cited by examiner

APPARATUS AND METHOD FOR DETERMINING OPTICAL RETARDATION AND BIREFRINGENCE

FIELD OF INVENTION

The present invention is generally related to the determination of the optical birefringence value of a material, and more particularly to an apparatus and method for determining the birefringence value of a polymeric material, for example, during its manufacture and using the determined value to control the manufacturing process.

BACKGROUND

Molecular orientation of a material may be dependent on process parameters such as time, temperature, draw-ratio, crystalline content, and the like. For example, it is generally known that drawing of a polymeric material leads to an increase in the molecular orientation of the material and hence the anisotropic mechanical properties of the material, such as its tensile strength, elongation, and rupture energy. In view of this, it is useful to identify the degree of molecular orientation of a material in order to study the effects of these process parameters on the type and degree of orientation, allowing scientists to better understand the molecular behavior and mechanical properties of the material. Further, obtaining the orientation information during processing in real-time, without removing the material from the production process, i.e., on-line, allows for instantaneous process control and optimization. Some benefits of instantaneous process monitoring include a reduced time to develop an optimized process, reduced material waste, and reduced variability in final product, all leading to a more efficient process. Real-time orientation information and on-line measurement are especially important for materials that are dimensionally and morphologically unstable (i.e., due to relaxation, crystallization, etc.), where the properties of the material may change due to changes in time, temperature, etc, for example, where changes in properties can occur in the short period of time it takes to remove the material from the manufacturing process to the location for evaluation of molecular orientation.

Birefringence, also known as double refraction, is a useful technique for measuring molecular orientation of a material, and thus is useful for studying structure-property relationships of various polymeric systems. For example, the effect of various process parameters can be evaluated directly by measuring birefringence. Over the past years, several techniques have been developed to measure this optical parameter. Such techniques include the use of isorefractive immersion fluids, a depolarized microscope with a compensator, a photographic interference fringe method, or even a depolarized monochromatic light source.

One well known technique for measuring the birefringence of a material is optical microscopy, which utilizes visible light having wavelengths in the range from about 400 to about 800 nm, to evaluate the molecular orientation of a material. This technique, which may be used to evaluate materials of various geometries such as planar films or cylindrical fibers, is described, for instance, by Yang et al, in J. Polym. Sci. Polym. Phys. Ed. 20, 981-987 (1982), where the birefringence of stationary fiber samples is measured using Babinet or Berek compensators. Additionally, GB 2,066,458 describes an optical microscopy system using a compensator for on-line measurement of birefringence of fibers in motion. One drawback with either compensator-based method is that measurements are not readily made on fibers in motion. Although GB 2,066,458 discloses an optical microscopy system for on-line measurement of birefringence, it is expected that visual observation of a moving fiber through a microscope is onerous because the fiber would be continuously moving in and out of focus, and the dark fringe that indicates the correct angle on the compensator would be difficult to assess for the moving fiber. In addition, compensator techniques fail on samples with very high or very low birefringence.

Several other techniques using interference-based optical microscopy for measurement of birefringence of fiber samples are described by Roche et al, in Fiber Prod. 12(1), 51-56 (1984) and Textile Res. J. 57, 371-378 (1987); Hamza et al, in Poly. Comm. 30, 186-189 (1989); and Yang et al, in Polym. Sci. Polym. Phys. Ed. 20, 981-987 (1982); and in GB 2,052,049. These techniques are useful for deconvoluting orientation across a fiber, but like the compensator-based methods, interference-based methods are unsuitable for on-line measurement of fibers since it is difficult to observe the interference fringes. For example, observing and counting the fringes may be difficult for a fiber in motion since the moving sample would blur the fringes and prevent fringe-counting.

There are additional drawbacks to using optical microscopy to measure the birefringence of a material. Another drawback is that use of optical microscopy to evaluate the molecular orientation of a sample is unsuitable for dyed materials, since the dye in a sample would absorb much of the spectra of light in the visible light range of wavelengths utilized in optical microscopy. Yet another drawback of using optical microscopy is that the birefringence of very low and very highly oriented materials cannot be evaluated, since there are few reference standards at very low or very high orders of retardation.

Other techniques for measuring the birefringence of a material using a visible light source have been disclosed, for example by Yang, Chouinard and Lingg, in Polym. Sci. Polym. Phys. Ed. 20, 981-987 (1982), who developed a method to measure birefringence of highly oriented fibers using a visible light source Beckman spectrophotometer. Hongladarom and Burghardt, Macromolecules, 26, 785 (1993), and Beekmans and de Boer, Macromolecules, 29, 8726 (1996), report a spectrographic birefringence technique for the determination of orientation of liquid crystalline polymers solutions having high anisotropy. This technique uses a multiwavelength white light source operating in the range of 500-700 nm. In this wavelength range the birefringence is wavelength dependent (known as birefringence dispersion). The birefringence dispersion is also material dependent. The variability of the birefringence dispersion was addressed by these authors several ways. First, the relative birefringence corresponding to a single wavelength (633 nm) is calculated either by fitting the observed spectra with an arbitrary set of equations containing several adjustable parameters (Hongladarom and Burghardt), or by determining the periods of oscillations over a short wavelength interval from which the birefringence is calculated (Beekmans and de Boer). The last method assumes that, for a given material, the birefringence does not change much between two subsequent zero crossings, which is generally not the case for this wavelength range used. Finally, since both approaches rely on normalized intensity measurements, these techniques are very sensitive to the changes in the thickness of the sample which can cause large errors in measuring birefringence. In addition, like the previously described methods using optical microscopy, the visible light spectrographic methods are not suitable for dyed materials.

Additional techniques using monochromatic light sources have been disclosed. Mortimer and Peguy, (Textile Res. J. 64(9), 544-551 (1994), built a device for on-line measurement of fiber birefringence, using a He—Ne, monochromatic laser (632.8 nm) source. U.S. Pat. No. 4,309,110 to Tumerman discloses an apparatus and method for determining optical properties of a substance by passing a beam of linearly polarized monochromatic light through the substance. The polarization vector of light is mechanically caused to rotate at a definite frequency, and the light is measured by a photodetector. The relative phase shift and/or modulation coefficient of this beam after passing through the substance is compared with a reference beam that has not passed through the substance, to effect measurement of linear and circular birefringence. Finally, U.S. Pat. No. 5,319,194 to Yoshizumi et al. discloses a method for measuring birefringence employing a laser that emits two beams at different frequencies. After the beams have passed through the sample, the beams are split by frequency and directed to two analyzers that are polarization sensitive. However, each of the monochromatic light source techniques described above is unsuitable for evaluating the birefringence value of highly oriented fibers where optical retardation can go to very high orders. Also, in laser-based techniques, when measuring small-diameter samples in motion, the signal becomes very erratic due to the moving laser-to-sample contact point.

Despite the teachings described above, there remains a need for a method and/or apparatus to measure the birefringence, both off-line and on-line, of an anisotropic material having very low or very high birefringence, that is not limited by the shape, form or geometric configuration of the material, or by whether the material is dyed or undyed.

SUMMARY

Described herein is a method for determining the optical retardation value of an anisotropic material utilizing a polarized light beam having at least a portion of the wavenumbers between about 4,000 to about 10,000 cm$^{-1}$. The polarized light beam is passed through the material to obtain a transmitted beam, which is then polarized and analyzed by Fourier transform near infrared (FT-NIR) detector operated in at least a portion of the range of wavenumbers between about 4,000 to about 10,000 cm$^{-1}$. An absorbance or transmission spectra is collected as a function of wavenumbers in at least a portion of the range between about 4,000 to about 10,000 cm$^{-1}$ and the optical retardation value of the material is calculated using the spectra.

Another embodiment is a method for determining the birefringence of the material from the optical retardation value.

An alternative embodiment is a method for optimizing a physical property of an anisotropic material by evaluating its birefringence.

Also described is a FT-NIR spectrophotometer and system for providing birefringence measurement, and a sample cell for use in combination with conventional FT-NIR spectrophotometers.

DETAILED DESCRIPTION

Figure 1:
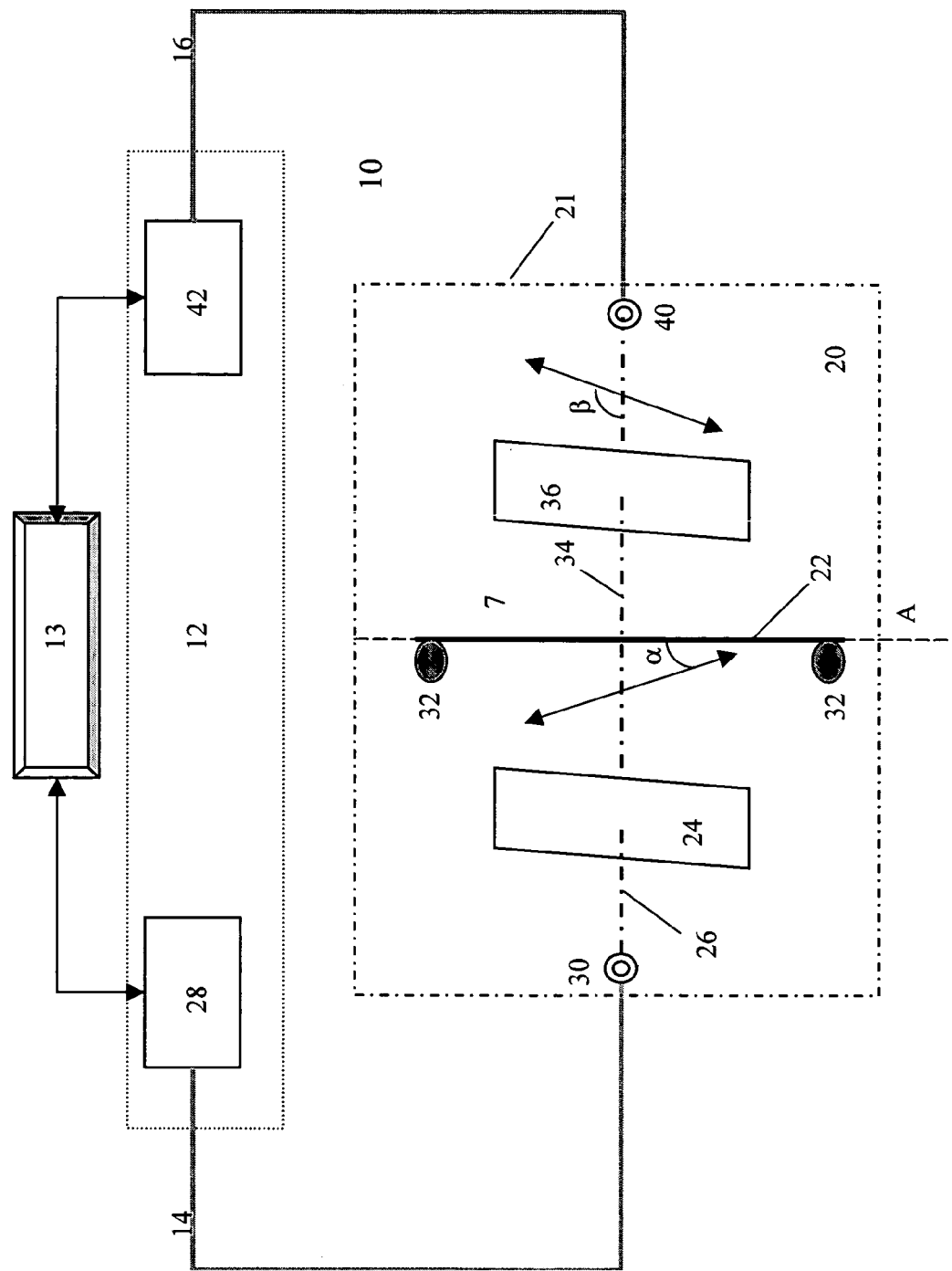
FIG. 1 is a schematic diagram of a Fourier transform near infrared-based system for determining optical retardation and birefringence values.

As light travels though an anisotropic material, the light undergoes a differential phase shift, $\Delta\phi$; which is directly related to the optical retardation value $\Delta nd$ for a given wavenumber $1/\lambda$ (where $\lambda$ is wavelength) according to formula (I):

$$\Delta\phi = 2\pi\Delta nd/\lambda \tag{I}$$

where $\Delta n$ is the birefringence value. The optical retardation value is the birefringence value multiplied by the optical path length, d, of the material. Materials exhibiting a high degree of orientation are expected to have a higher birefringence value than materials exhibiting a lesser degree of orientation. For example, materials that are isotropic or unoriented are expected to exhibit no birefringence and their optical retardation value is expected to be zero.

According to one embodiment of the invention, an anisotropic material is placed between two optical-grade, crossed polarizers, each preferably disposed at 45° from the material's orientation axis so that collectively, the planes of polarization between the polarizers are 90° apart. A near infrared light beam is passed through a first polarizer, where the light becomes linearly polarized, followed by passage through the anisotropic material. As the near infrared light beam travels through the material, the material absorbs and scatters various wavelengths of the light at different intensities. Depending upon the degree of molecular orientation of the material, certain wavelengths of the light beam are absorbed while other wavelengths are scattered and exit the material. The scattered spectra of light exiting the material is collected by a detector and the absorbance of the spectra of scattered light (or transmission) is plotted as a function of wavenumber (cm$^{-1}$). The plot that is generated has a series of peaks, which represents the maximum absorbance (or transmission) for a given wavenumber. Each sequential peak may then be assigned a sequential whole number, m, that may be plotted in a second plot as a function of the wavenumber associated with that peak. The slope of the relationship between the whole number assigned to each peak and the corresponding wavenumber gives the optical retardation value. For example formula (I), which may be rewritten as formula (II):

$$\Delta\phi/2\pi = \Delta nd/\lambda \tag{II}$$

may be used to obtain the optical retardation value $\Delta nd$ of the material, which corresponds to the slope of the plot of m, where m=(Δϕ/2π), as a function of the wavenumber associated with that peak, where the wavenumber=(1/λ). The optical retardation value may then be divided by the optical path length of the material to obtain the birefringence value, i.e., if the material is a fiber, the optical path length of the material is the diameter of the fiber (which may be measured using an on-line laser micrometer). Once the birefringence value is established for a material, it may then be compared against a third plot of a physical property parameter, such as stress at maximum load, as a function of birefringence and a process control parameter, such as draw ratio of extrusion. By making this comparison, it is possible to optimize the physical property parameter of a product by adjusting the process control parameter to the value corresponding to the desired value of the physical property parameter shown in the third plot.

Referring to FIG. 1, a schematic FT-NIR-based system 10 includes a FT-NIR spectrophotometer 12 that may be controlled by computer 13 disposed to accept fiber optic cables. System 10 includes a first polarizer 24 for polarizing a light beam 26 that is produced by a source 28, preferably a component of FT-NIR spectrophotometer 12. Light beam 26 is polarized by first polarizer 24 in a plane a that is disposed preferably substantially 45° from an axis of orientation "A" of material 22. Light beam 26 preferably is passed through a collimator lens 30 prior to polarizer 24. System 10 further includes a sample holder 32 positioned to hold the material 22 in a position relative to light beam 26. Light beam 26 includes at least a portion of the spectral range between about 4000 cm$^{-1}$ and 10,000 cm$^{-1}$ and is of sufficient intensity that, when applied to material 22 substantially perpendicular to the surface of the material, passes through the material to provide a transmitted beam 34. Transmitted beam 34 is directed to a second polarizer 36 disposed to polarize beam 34 in a plane β preferably substantially 90° removed from the plane of polarization of first polarizer 24. Preferably, transmitted beam 34 is passed through a collimator lens 40 prior to being directed to detector or analyzer 42, preferably a component of FT-NIR spectrophotometer 12.

As discussed above, for a dimensionally and morphologically unstable material (i.e., due to relaxation, crystallization, etc.), the properties of the material change in the short period of time to go from on-line to off-line, due to changes in time, temperature, etc. Therefore, it is desirable to measure the birefringence of a dimensionally and morphologically unstable material on-line in accordance with the embodiments described herein. When measuring the birefringence on-line, stage 20, with polarizers 24 and 36, collimators 30 and 40, and sample holder 32 is positioned in-line with the material 22, and connected to spectrophotometer 12 with fiber optic cables 14 and 16. In this fashion, stage 20 with the components described above functions as a remote sample cell 21. For particular applications, spectrophotometer 12 may be adapted to receive a plurality of cables 14 and 16 so that a plurality of sample cells 21 could be disposed in-line along one or more production lines. Sample cell 21 may include fittings to facilitate mounting, covers to protect the optical components and path and the like. Sample holder 32 may include rollers or adjustments to facilitate placement of a moving sample material between polarizers 24 and 36 and in the path of light beam 26. The phrase "substantially remote" is used to describe the relative position of the sample cell 21 to the FT-NIR spectrophotometer 12, and includes all positions where the sample cell is not contained in the FT-NIR spectrophotometer. Alternatively, stage 20 (optionally having fiber optic cables 14 and 16) may be contained in spectrophotometer 12.

Figure 2:
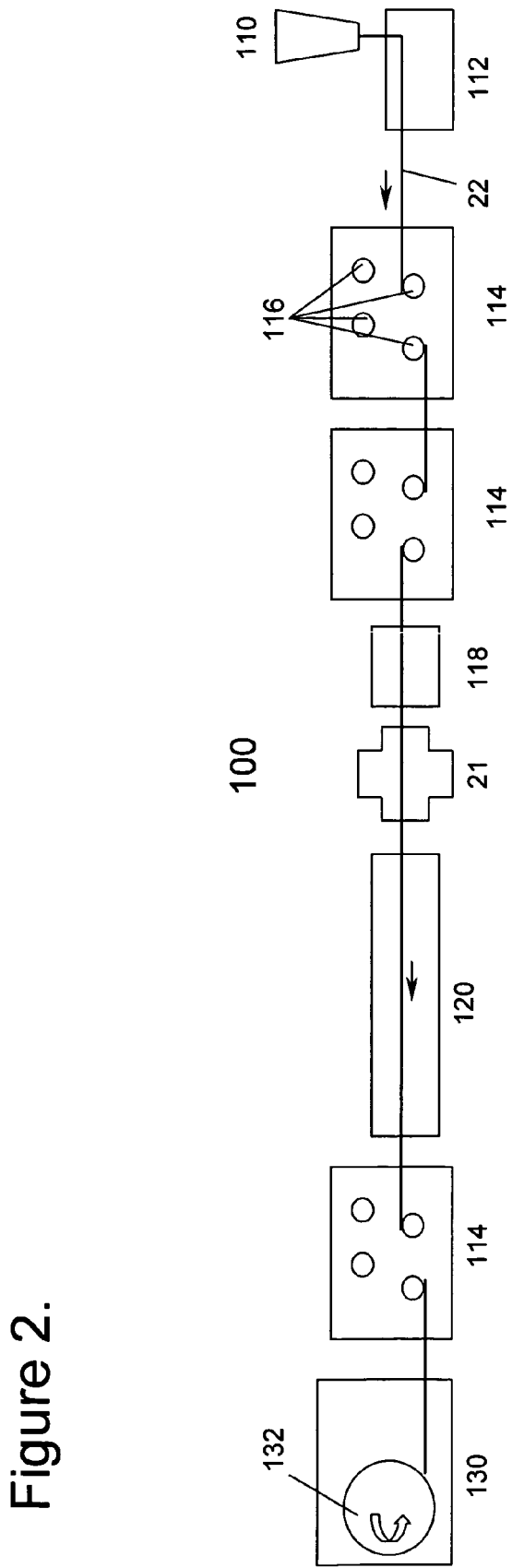
FIG. 2 is a schematic diagram of a typical fiber extrusion process.

During a fiber extrusion process, for example, one or more sample cell 21 may be placed on-line at different locations, preferably between different drawing stages. It should be noted that the sample cell and apparatus are non-destructive and non-interruptive of the process flow. Referring to FIG. 2, a typical fiber extrusion line 100 is illustrated. Extrusion line 100 includes an extruder 110 that extrudes fiber 22. The machine direction of fiber 22 through extrusion line 100 is illustrated by arrows. Fiber 22 is passed through a water bath 112 onto a first godet station 114. A godet station typically has a plurality of rollers 116 that are individually rotated. Rollers 116 generally rotate at different speeds with respect to one another. Some of them are heated to facilitate the drawing process. When the rollers 116 are sequentially rotated at increasing speeds, fiber 22 is stretched between them, thus providing an orientation to fiber 22. In the example provided here, there are three godet stations 114. Following the first godet station, a second godet station is provided. After the second godet station, a laser micrometer 118 is positioned to determine the diameter of fiber 22. After laser micrometer station 118, sample cell 21 of the invention is positioned with fiber 22 passing through. Sample cell 21 is connected to the FT-NIR spectrophotometer with the source and detector or analyzer by fiber optic cables. The output from the laser micrometer is provided to a computer used to monitor the output of the spectrophotometer. Laser micrometer 118 may be positioned either immediately before or after sample cell 21, so that the diameter of the fiber in the sample cell 21 is more accurately determined. Fiber extrusion line 100 also may include an annealing oven 120, another godet station and a winding station 130 for collecting fiber 22 on a suitable roll 132. For particular applications, one or more sample cells 21 may be positioned along the line between or after the godet station 114 after the annealing oven 120. Preferably, each of the sample cells 21 includes a laser micrometer station 118 for determination of the fiber diameter. The birefringence measurement may then coupled by the computer to the speed control of the godet stations and used to adjust the relative speed of the rollers 116 so that a physical property that is correlated to the degree of fiber orientation may be optimized.

Spectra of scattered light exiting the material held in or in motion through the sample cell may be collected at intervals of time ranging from 0 to 3600 seconds, with an overall scanning time of about 1 to 120 seconds. When measuring the birefringence of a material on-line, shorter scanning times are preferred, providing faster real-time information.

Anisotropic materials that may be evaluated herein include, but are not limited to polymeric films, fibers or liquid crystals, each of which may be dyed or undyed, and including anisotropic materials have very low or very high orders of retardation. As discussed above, an advantage of the method and/or apparatus described herein is their use on-line for fibers, such as small diameter fibers ranging from about 1 mil (0.0254 mm) to macroscopic size, i.e., 200 mil (~5 mm), preferably ranging from about 1 mil to 100 mil, that are dimensionally and morphologically stable or unstable.

Physical properties that may be optimized with the method and/or apparatus described herein include any property that is correlated to molecular orientation, including but not limited to mechanical strength, including but not limited to breaking strength retention, knot strength, stress at maximum load, maximum elongation and Young's Modulus (stress/strain), transparency, bioabsorption rate, and in the case where the material comprises a therapeutic agent, a therapeutic agent release profile.

Finally the process parameters that may be controlled by evaluating the birefringence of a material are those parameters that correlate to molecular orientation, including but not limited to temperature of various processing steps, degree of drawing/stretching/mechanical deforming of the material being processed, and the mixing rate of additives (such as bioactive agents).

The method and/or apparatus described herein provide the ability to monitor the production of oriented polymeric materials by real-time measurement of the birefringence of the material as it is being produced. The measurement is both non-destructive and non-interruptive of the process flow. Hence, real-time adjustments may be made to the production process to keep a desired property within an acceptable range by measuring the birefringence, thereby improving efficiency of the process.

EXAMPLE 1

Off-Line Evaluation of Birefringence by Optical Microscopy (OM) and FT-NIR

The birefringence of commercially available Monocryl™ and Vicryl™ fibers were made off-line using the method described herein and off-line with a conventional depolarized optical microscope equipped with a multiple order compensator. Tensile properties of the samples were also investigated using a Instron testing machine. These data are presented in Table 1.

TABLE 1

Off-line comparison study of physical properties of two polyester based fibers

|  | Monocryl | | | | | Vicryl | | |
| --- | --- | --- | --- | --- | --- | --- | --- | --- |
| Draw Ratio | 8 | 7.5 | 6.5 | 5.5 | 6 | 5.5 | 5 | 4.5 |
| Diameter (mils) | 9.09 | 9.04 | 8.88 | 8.96 | 8.8 | 8.86 | 8.73 | 8.79 |
| BS (lbs) | 9.89 | 9.53 | 6.51 | 3.83 | 5.38 | 4.96 | 4.62 | 3.96 |
| Stress at Max (kpsi) | 152.37 | 148.51 | 105.19 | 60.64 | 88.47 | 80.6 | 77.2 | 65.35 |
| Elongation (%) | 31.24 | 31.56 | 46.09 | 74.79 | 27.79 | 33.59 | 42.21 | 52.38 |
| Young's Modulus (kpsi) | 123.1 | 139.1 | 66.1 | 51 | 1216.6 | 1119.5 | 1043.8 | 934.4 |
| (O-M) Birefringence | 0.069 | 0.067 | 0.059 | 0.051 | 0.058 | 0.054 | 0.051 | 0.046 |
| (FT-NIR) Birefringence | 0.071 | 0.069 | 0.062 | 0.054 | 0.060 | 0.056 | 0.052 | 0.047 |

The results shown in Table 1 indicate substantial agreement in the birefringence values measured using optical microscopy (OM) and the method and apparatus described herein. The data also indicates that an increase in draw ratio caused a substantial and systematic increase of both birefringence and various mechanical strength properties identified in Table 1.

EXAMPLE 2

Off-Line Evaluation of Birefringence of Different Undyed and Dyed Samples by FT-NIR Most conventional techniques used for measuring birefringence, including OM, cannot be used for measuring the birefringence of dyed samples, because the presence of the dye, which absorbs certain wavelengths in the visible spectrum, confounds the optical retardation measurement. Unlike the conventional methods, the method and apparatus described herein may be used to determine the birefringence of a dyed sample. Data summarized in Table 2 indicate clearly that method described herein can effectively measure different dyed materials, stretched and unstretched with a wide range of different fiber sizes.

TABLE 2

Off-line FT-NIR birefringence study of different polymeric materials

| Material | Thickness (mils) | Process | Birefingence |
| --- | --- | --- | --- |
| FAM-fiber | 9.84 | drawn | 0.066 |
| PP fiber-dyed | 16.1 | undrawn | 0.013 |
| PP fiber-dyed | 7.1 | drawn | 0.037 |
| PP fiber | 12.5 | drawn 9× | 0.031 |
| PDS-fiber-dyed | 13.6 | drawn | 0.066 |
| PDS-film | 12.6 | unstreteched | 0.002 |
| PDS-film | 7.9 | streched | 0.023 |

Figure 3:
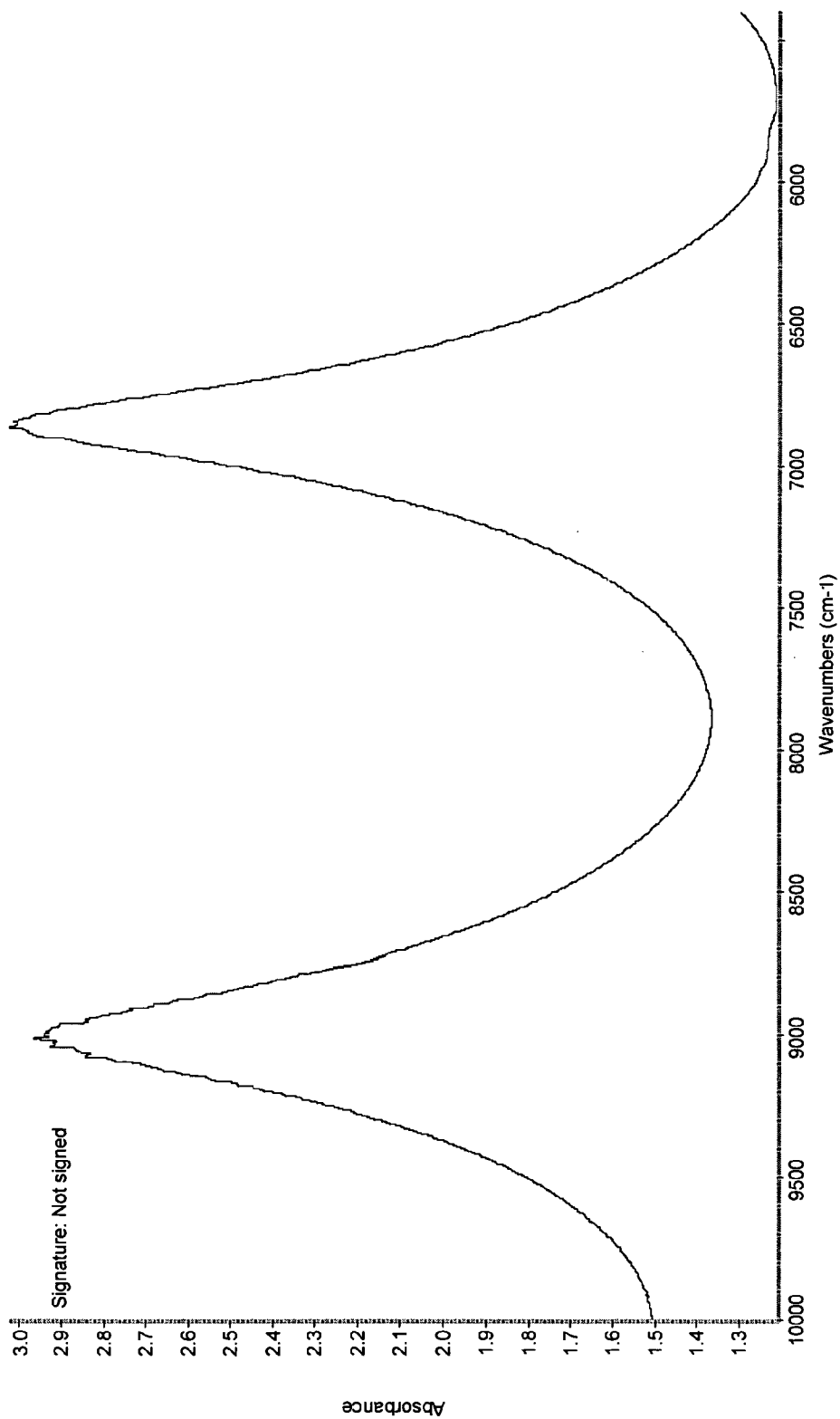
FIG. 3 is an FT-NIR spectra of a drawn dyed poly(p-dioxanone) (PDS) film.
Figure 4:
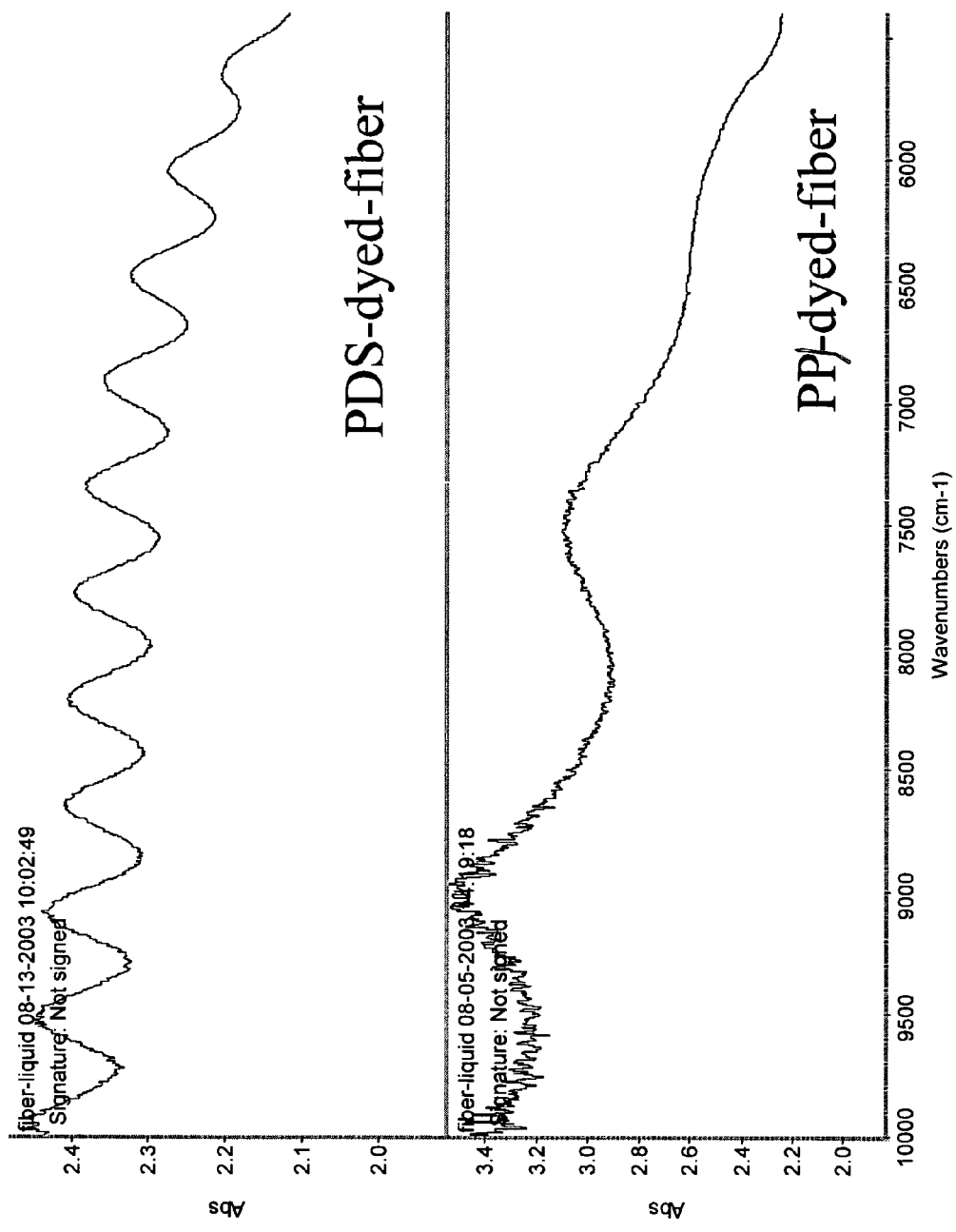
FIG. 4 is an FT-NIR spectra of drawn dyed PDS and polypropylene fibers.

FT-NIR spectra obtained on dyed poly(p-dioxanone) (PDS) stretched film and PDS and polypropylene (PP) drawn fibers (both dyed) are shown in FIGS. 3 and 4, respectively.

EXAMPLE 3

On-Line Evaluation of Birefringence by FT-NIR: Sample Calculation

Figure 5A:
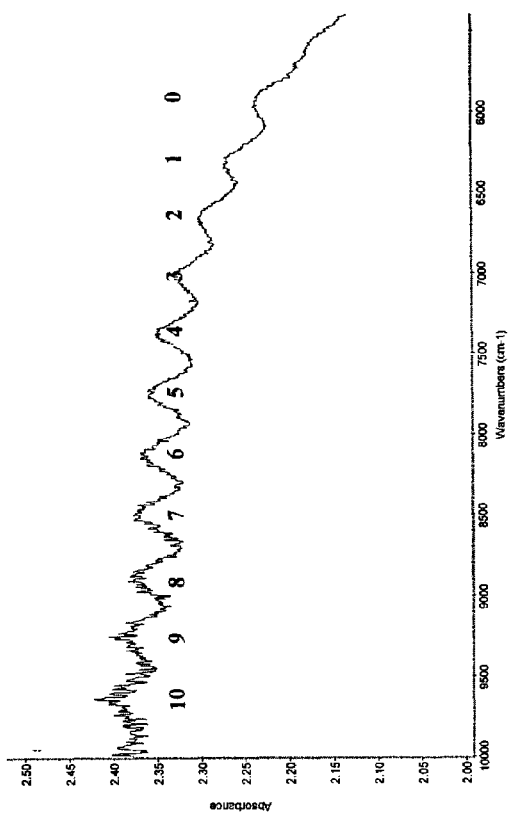
FIG. 5A-B is a graphical illustration of a birefringence calculation.
Figure 5B:
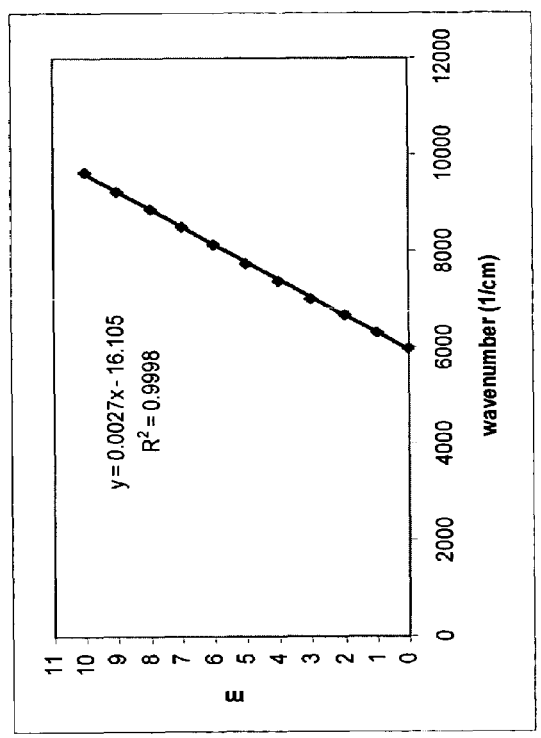

The spectral information illustrated in FIG. 5A was obtained during real-time on-line monofilament fiber extrusion of a terpolymer of glycolide-ε-caprolactone-PDS using a draw ratio of 8.33×. Each of the birefringence peaks is assigned a value from zero to some whole value m, i.e., 0 through 10. In FIG. 5B, the integer m is plotted as a function of wavenumber corresponding to the peak corresponding to that integer. This plot reveals that the peaks are equally spaced, so that only two adjacent peaks are needed to compute the slope. It should be noted that this feature is not true for spectrophotometers operating in wavelength regions outside the NIR range due to birefringence dispersion (as mentioned previously for UV/Visible light instruments). The calculated slope of the curve in FIG. 5B, 0.0027, is then divided by the sample diameter of 14 mils (obtained from on-line laser micrometer measurements) to obtain a birefringence value of 0.0764.

EXAMPLE 4

On-Line Evaluation of Birefringence by FT-NIR

Effect of Different Godet Speed (Draw Ratio)

Sample cell 21 was placed after the second set of godets in FIG. 2. A sample cell placed after the water bath 112 in FIG. 2 verified that no orientation occurred at that stage of extrusion line 100. Varying the godet speed caused a systematic change in the fiber draw ratios that, in turn greatly affected the birefringence values. Real-time, on-line FT-NIR birefringence data obtained during fiber drawing of a terpolymer of glycolide-ε-caprolactone-PDS are presented in Table 3. The measurements of the mechanical tensile properties of the fiber that are shown in the table were made off-line.

TABLE 3

Effect of draw ratio on physical properties of fiber during extrusion Drawn (Position 2)

| Draw Ratio | 5 | 5.74 | 6.67 | 7.59 | 7.96 | 8.33 |
|---|---|---|---|---|---|---|
| Diameter (mils) | 18 | 17.5 | 14.4 | 14.1 | 13.5 | 14.04 |
| BS (lbs) | 7.87 | 8.35 | 9.85 | 11.03 | 13.75 | 16.73 |
| Stress at Max (kpsi) | 41.11 | 45.73 | 60.71 | 71.82 | 91.73 | 108.97 |
| Elongation (%) | 102.18 | 90.1 | 66.48 | 42.04 | 33.02 | 31.16 |
| Young's Modulus (kpsi) | 53.6 | 58.4 | 66 | 77.9 | 95 | 102.9 |
| (FT-NIR) Birefringence | 0.016 | 0.024 | 0.030 | 0.048 | 0.062 | 0.077 |

Figure 6:
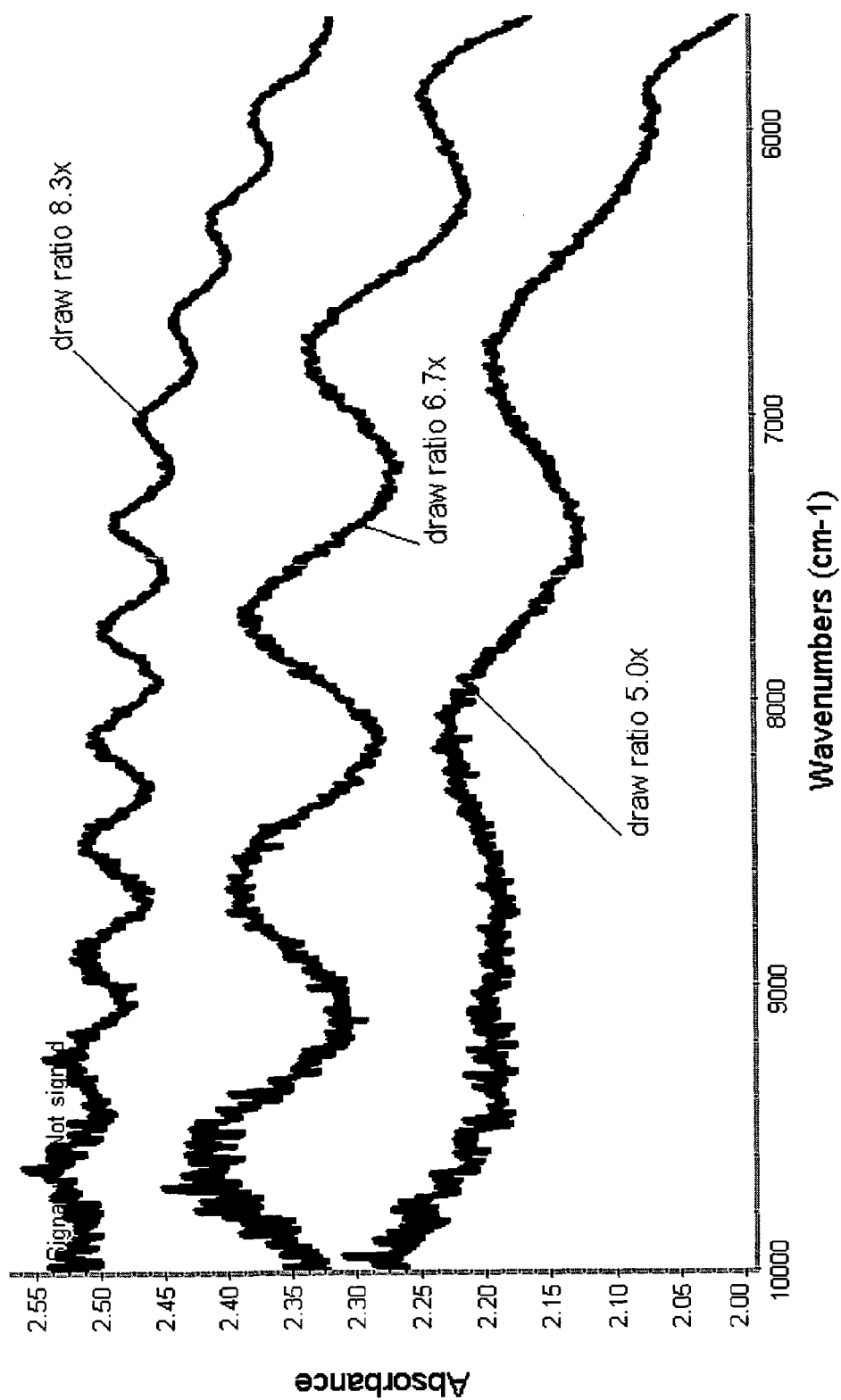
FIG. 6 are FT-NIR spectra of a terpolymer of glycolide-ε-caprolactone-PDS fiber obtained on-line during extrusion utilizing different draw ratios.
Figure 7A:
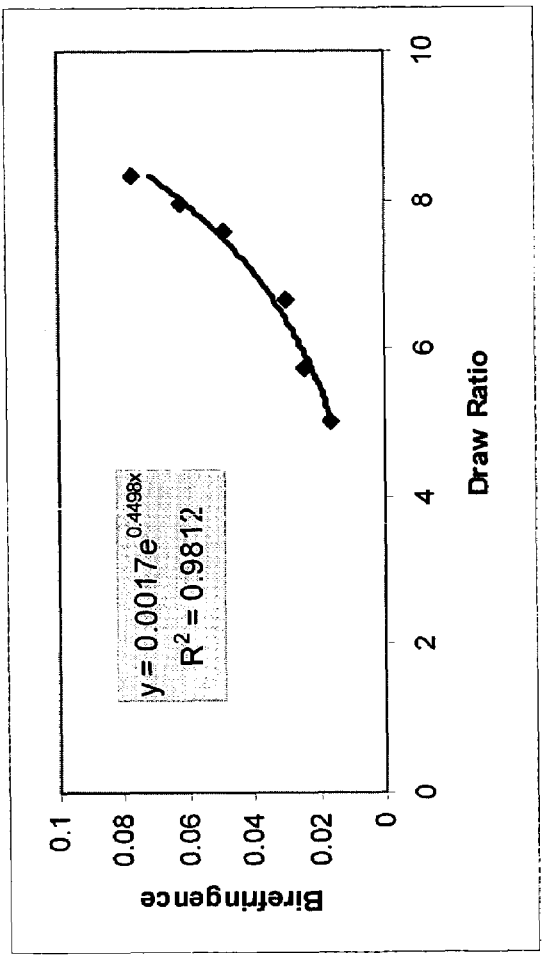
FIG. 7A-B is draw ratio of a terpolymer of glycolide-ε-caprolactone-PDS fiber obtained on-line during extrusion as a function of A) FT-NIR birefringence and B) stress at maximum load obtained from off-line Instron testing measurements.
Figure 7B:
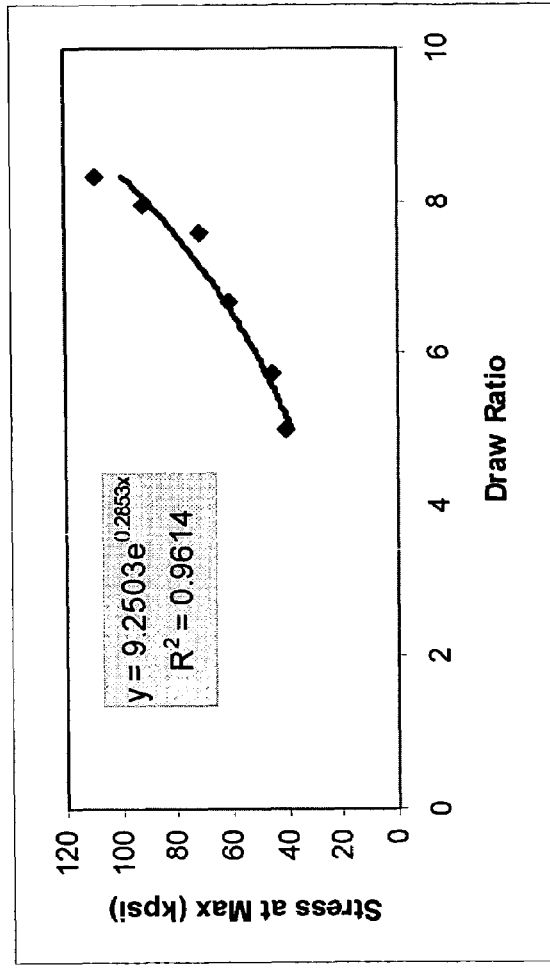
Figure 8:
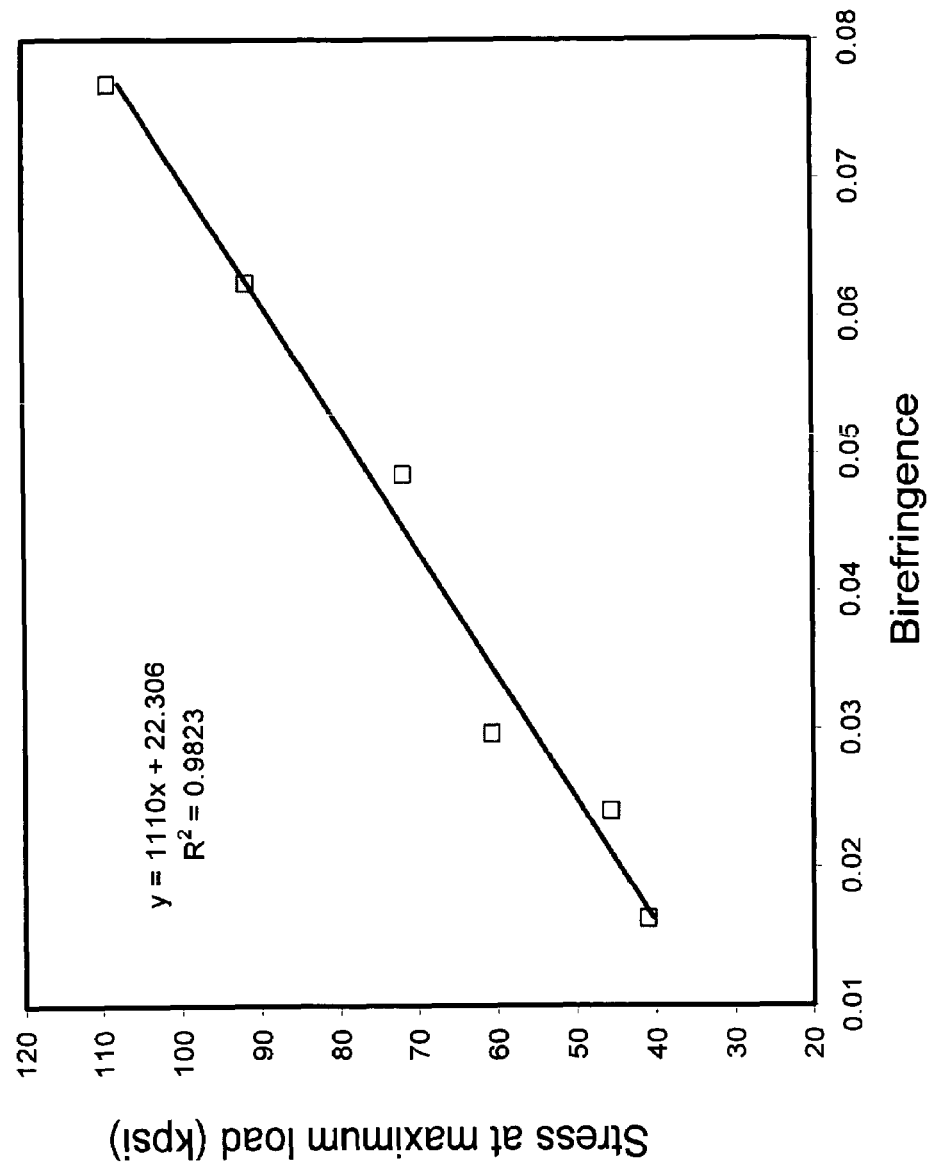
FIG. 8 is stress at maximum load obtained from off-line Instron testing measurements as a function of FT-NIR birefringence (measured on-line).

FIG. 6 presents a series of FT-NIR signals obtained during real-time, on-line extrusion of a terpolymer of glycolide-α-caprolactone-PDS as a function of different draw ratios. The overall scanning time was about 4 seconds. The effect of draw ratio on birefringence and mechanical strength of the fiber is illustrated in FIGS. 7A-B. From these two figures it is demonstrated that an increase in the draw ratio caused very similar functional dependence effects on both birefringence and mechanical strength properties. Furthermore, we found that mechanical strength is directly proportional to the birefringence signal as illustrated in FIG. 8. This finding allows the use of on-line evaluation of birefringence to predict and control mechanical properties of a drawn fiber in real processing time.

EXAMPLE 5

On-Line Evaluation of Birefringence by FT-NIR

Effect of Different Oven Annealing Temperatures

Sample cell 21 was positioned after the annealing oven 120 in extrusion line 100 of FIG. 2. A FT-NIR signal was evaluated in real-time after applying different oven temperatures. These data are summarized in Table 4.

TABLE 4

Effect of annealing temperature on physical properties of a terpolymer of glycolide-ε-caprolactone-PDS fiber during extrusion using a constant draw ratio of 7.59. Drawn at 7.59 (Position 3)

| Oven Temperature (° F.) | 75 | 100 | 120 | 140 | 160 |
|---|---|---|---|---|---|
| Diameter (mils) | 14 | 14 | 14.1 | 14 | 14 |
| BS (lbs) | 10.49 | 10.72 | 10.11 | 10.48 | 11.14 |
| Stress at Max (kpsi) | 71.11 | 71.17 | 68.99 | 72.22 | 72.96 |
| Elongation (%) | 42.34 | 41.17 | 40.26 | 41.77 | 41.38 |
| Young's Modulus (kpsi) | 80.8 | 77.3 | 84.3 | 87.1 | 94.2 |
| (FT-NIR) Birefringence | 0.049 | 0.050 | 0.053 | 0.054 | 0.055 |

Only a slight but systematic effect of oven temperature on the birefringence value was observed. With an increase in oven temperature from room temperature to 160° F., birefringence gradually increased from 0.049 to 0.055. At the same time, off-line measurements of mechanical data show certain oscillation, due to its inherently lower precision and reproducibility features.

EXAMPLE 6

On-Line Evaluation of Birefringence by FT-NIR

Investigation of Reproducibility of FT-NIR Birefringence

Reproducibility and precision of the method and apparatus described herein was observed. Ten consecutive measurements were made and birefringence values recorded during on-line fiber extrusion. These data are shown in Table 5.

TABLE 5

Birefringence values of ten consecutive measurements of a terpolymer of glycolide-ε-caprolactone-PDS fiber during real-time, on-line extrusion utilizing a draw ratio of 7.59x.

| Run # | (FT-NIR) Birefringence |
|---|---|
| 1 | 0.055 |
| 2 | 0.055 |
| 3 | 0.055 |
| 4 | 0.054 |
| 5 | 0.055 |
| 6 | 0.055 |
| 7 | 0.055 |
| 8 | 0.054 |
| 9 | 0.054 |
| 10 | 0.055 |
| mean | 0.054726 |
| stdev | 0.000484 |
| % dev (Biref) | 0.885 |
| % dev (instron) | 7.200 |

A standard deviation of 0.88% shows the performance of the FT-NIR birefringence evaluation technique described herein, which is significantly better than currently used off-line tensile testing standard deviation values, i.e., as high as 7.2% using substantially the same processing conditions.

What is claimed is:

1. A method for producing an anisotropic material having a first physical property comprising:
   (a) determining the optical retardation value of the anisotropic material, said step of determining the optical retardation value comprising:
   polarizing a light beam having at least a portion of the wavenumbers between about 4,000 to about 10,000 $cm^{-1}$ to obtain a polarized light beam;
   passing the polarized light beam through the material to obtain a transmitted beam;
   polarizing the transmitted beam to obtain a polarized transmitted beam;
   detecting the polarized transmitted beam;
   collecting an absorbance or transmission spectra as a function of wavenumbers; and
   calculating the optical retardation value of the material using the spectra;
   (b) monitoring the optical retardation value determined in step (a); and
   (c) adjusting a process parameter using the optical retardation value monitored in step (b) to optimize the first physical property of the material.

2. A method for producing an anisotropic material having a first physical property comprising:
   (a) determining the birefringence value of the anisotropic material having at least one thickness, comprising:
   polarizing a light beam having at least a portion of the wavenumbers between about 4,000 to about 10,000 $cm^{-1}$ to obtain a polarized light beam;
   passing the polarized light beam through the material to obtain a transmitted beam;

polarizing the transmitted beam to obtain a polarized transmitted beam;

detecting the polarized transmitted beam;

collecting an absorbance or transmission spectra as a function of wavenumbers; p1 calculating the optical retardation value of the material using the spectra; and determining the birefringence value of the material according to the formula:

$$R = \Delta n d$$

where R=optical retardation value, $\Delta n$ is the birefringence value and d is the thickness of the material; and (b) monitoring the birefringence value determined in step (a); and (c) adjusting a process parameter using the birefringence value monitored in step (b) to optimize the first physical property of the material.

3. A method of optimizing a first physical property of an anisotropic material during its manufacture comprising:

polarizing a light beam having at least a portion of the wavenumbers between about 4,000 to about 10,000 cm$^{-1}$ to obtain a polarized light beam;

passing the polarized light beam through the material to obtain a transmitted beam;

polarizing the transmitted beam to obtain a polarized transmitted beam; detecting the polarized transmitted beam;

collecting an absorbance or transmission spectra as a function of wavenumbers, calculating the optical retardation value of the material using the spectra; determining the birefringence value of the material according to the formula:

$$R = \Delta n_{sample} d$$

where R=optical retardation value, $\Delta n_{sample}$, is the birefringence value and d is the thickness of the material;

locating the value of $\Delta n_{sample}$ on a previously prepared curve of the first physical property of the material plotted as functions of birefringence and a first process parameter;

identifying an initial first physical property and initial first process parameter associated with $\Delta n_{sample}$;

selecting a desired value for the first physical property of the anisotropic material and identifying the target first process parameter corresponding to the desired value on the previously prepared curve; and adjusting the initial first process parameter to the target first process parameter to optimize the first physical property of the material.

4. The method of claim 1, 2 or 3 where the step of collecting the absorbance or transmission spectra as a function of wavenumbers further comprises generating a series of peak maxima; and the step of calculating the optical retardation value of the material using the spectra comprises using the location of peak maxima.

5. The method of claim 4 where the step of calculating the optical retardation of the material using the location of peak maxima comprises assigning an order value to at least two successive peak maxima in the series;

determining the wavenumbers that correspond to the at least two successive peak maxima in the series; and establishing the slope of the linear relationship between the order values of the at least two consecutive peak maxima and the wavenumbers corresponding to those maxima, to obtain the optical retardation value.

6. The method of claim 3, where the step of passing the polarized light through the material is performed on-line or off-line.

7. The method of claim 6 where the step of passing the polarized light through the material is performed on-line and the material is a polymeric fiber having fiber diameter ranging from 1 to 100 mils.

8. The method of claim 1, 2 or 3 where the material has at least one axis of orientation and the light beam is polarized at 45° degrees from the orientation axis of the material.

9. The method of claim 8, where the transmitted beam is polarized in a plane disposed substantially perpendicular to the first plane.

10. The method of claim 1, 2 or 3 where the polarized light beam initially contacts the material substantially perpendicular to the axis of orientation of the material.

11. The method of claim 1, 2 or 3 where the material is selected from the group consisting of a polymeric film, a fiber or a liquid crystal.

12. The method of claim 3 where the first physical property is selected from the group consisting of breaking strength retention, knot strength, stress at maximum load, transparency, maximum elongation, Young's Modulus (stress/strain), bioabsorption rate, and therapeutic agent release profile.

13. The method of claim 3 where the first process parameter is selected from the group consisting of draw ratio, annealing oven temperature, godet speed, and extrusion throughput.

14. A Fourier transform near infrared spectrophotometer comprising:

source means for generating a light beam having at least a spectral range between about 4000 cm$^{-1}$ and 10,000 cm$^{-1}$;

first polarizer means for polarizing the light beam in a first plane to produce a polarized light beam;

holder means for holding a material in the path of the polarized light beam so that at least a portion of the polarized light beam is transmitted though the material as a transmitted beam;

second polarizer means for polarizing the transmitted beam in a second plane substantially 90 degrees to the first plane to produce a polarized transmitted beam; and detector means for receiving the polarized transmitted beam.

15. A Fourier transform near infrared based system comprising:

a Fourier transform near infrared spectrophotometer having source means for generating a light beam having at least a spectral range between about 4000 cm$^{-1}$ and 10,000 cm$^{-1}$ and detector means; and a sample cell comprising first polarizer means for polarizing the light beam in a first plane to produce a polarized light beam; holder means for holding a material in the path of the polarized light beam so that at least a portion of the polarized light beam is transmitted though the material as a transmitted beam; and second polarizer means for polarizing the transmitted beam in a second plane substantially 90 degrees to the first plane to produce a polarized transmitted beam;

wherein the polarized transmitted beam is directed to the detector means of the FT-NIR spectrophotometer and the sample cell is substantially remote to the FT-NIR spectrophotometer.

* * * * *